United States Patent
Zhao et al.

(10) Patent No.: US 12,144,298 B2
(45) Date of Patent: Nov. 19, 2024

(54) SEMI-DOMINANT MOLECULAR MARKER RELATED TO MAIZE DWARF AND APPLICATION THEREOF

(71) Applicants: Anhui Agricultural University, Anhui (CN); China National Seed Group Co., Ltd., Hainan (CN)

(72) Inventors: Yang Zhao, Anhui (CN); Qing Ma, Anhui (CN); Xiaoduo Lu, Anhui (CN); Yixiao Wang, Anhui (CN); Hongying Wu, Anhui (CN)

(73) Assignees: Anhui Agricultural University, Hefei (CN); China National Seed Group Co., Ltd., Sanya (CN)

( * ) Notice: Subject to any disclaimer, the term of this patent is extended or adjusted under 35 U.S.C. 154(b) by 0 days.

(21) Appl. No.: 18/233,341

(22) Filed: Aug. 14, 2023

(65) Prior Publication Data

US 2024/0114861 A1    Apr. 11, 2024

Related U.S. Application Data

(63) Continuation of application No. PCT/CN2023/099574, filed on Jun. 12, 2023.

(30) Foreign Application Priority Data

Oct. 10, 2022 (CN) .......................... 202211232107.X

(51) Int. Cl.
C12Q 1/68 (2018.01)
A01H 1/04 (2006.01)
C12Q 1/6895 (2018.01)

(52) U.S. Cl.
CPC .......... A01H 1/045 (2021.01); C12Q 1/6895 (2013.01); C12Q 2600/13 (2013.01); C12Q 2600/156 (2013.01)

(58) Field of Classification Search
None
See application file for complete search history.

(56) References Cited

U.S. PATENT DOCUMENTS 7,557,266 B2 * 7/2009 Lawit ................. C12N 15/8261
800/312
2020/0199609 A1 6/2020 Gao et al.

FOREIGN PATENT DOCUMENTS

| CN | 101479294 A | 7/2009 |
| CN | 113481315 A | 10/2021 |
| CN | 113788889 A | 12/2021 |
| WO | 2007124312 A2 | 11/2007 |

OTHER PUBLICATIONS

Notice of Allowance of counterpart Chinese Patent Application No. 202211232107.X issued on Apr. 26, 2023.
Yajie Ma et al., Genetic basis and molecular mechanisms of maize plant height and panicle height, Chinese Bioengineering Journal China Biotechnology, 2021, pp. 61-73, vol. 41, No. 12.
Yang Zhao et al., Genome-wide association study of maize plant architecture using F1 populations, Plant Molecular Biology, Dec. 5, 2018, pp. 1-15, vol. 99.
Shai J. Lawit et al., Maize DELLA Proteins dwarf plant8 and dwarf plant9 as Modulators of Plant Development, Plant Cell Physiol., 2010, pp. 1854-1868, vol. 51, No. 11.
1st search report of counterpart Chinese Patent Application No. 202211232107.X issued on Apr. 18, 2023.
D.N. Duvick, Genetic Progress in Yield of United States Maize (Zea mays L.), Maydica, 2005, pp. 193-202, vol. 50.
A. Sasaki et al., A mutant gibberellin-synthesis gene in rice, Nature, Apr. 18, 2002, pp. 701-702, vol. 416.
Jinrong Peng et al., 'Green revolution' genes encode mutant gibberellin response modulators, Nature, Jul. 15, 1999, pp. 256-261, vol. 400.
Kenji Gomi et al., GID2, an F-box subunit of the SCF E3 complex, specifically interacts with phosphorylated SLR1 protein and regulates the gibberellin-dependent degradation of SLR1 in rice, The Plant Journal, 2004, pp. 626-634, vol. 37.
Marcia Margis-Pinheiro et al., Isolation and characterization of a Ds-tagged rice (Oryza sativa L.) GA-responsive dwarf mutant defective in an early step of the gibberellin biosynthesis pathway, Plant Cell Rep, Jan. 25, 2005, pp. 819-833, vol. 23.
Akira Ikeda et al., slender Rice, a Constitutive Gibberellin Response Mutant, Is Caused by a Null Mutation of the SLR1 Gene, an Ortholog of the Height-Regulating Gene GAI/RGA/RHT/D8, The Plant Cell, May 2001, pp. 999-1010, vol. 13.
Rodney G. Winkler et al., The Maize Dwarf3 Gene Encodes a Cytochrome P450-Mediated Early Step in Gibberellin Biosynthesis, The Plant Cell, Aug. 1995, pp. 1307-1317, vol. 7.
Robert J. Bensen et al., Cloning and Characterization of the Maize An1 Gene, The Plant Cell, Jan. 1995, pp. 75-84, vol. 7.

(Continued)

Primary Examiner — Medina A Ibrahim

(57) ABSTRACT

The present application discloses a semi-dominant molecular marker related to maize dwarf and an application thereof, and relates to the technical field of maize molecular breeding. The molecular marker related to the maize dwarf is caused by a non-synonymous mutation from G to A in a maize gene Zm00001d013465, and the molecular marker is a nucleotide sequence composed of the non-synonymous mutation site and its upstream and downstream bases. The present application identifies a dwarf mutant, coded as E5779, from an EMS mutation population with maize B73 as the genetic background. By genome resequencing and Mutmap mapping, it is found that the mutant is caused by the non-synonymous mutation from G to A in the gene Zm00001d013465. The molecular marker is developed based on this, and the analysis and utilization of E5779 are helpful to improve the maize plant height and density-tolerant breeding, it has an important breeding application potential.

6 Claims, 3 Drawing Sheets

Specification includes a Sequence Listing.

(56) References Cited

OTHER PUBLICATIONS

Xingen Zhang et al., Comparative Transcriptomics Reveals the Molecular Mechanism of the Parental Lines of Maize Hybrid An'nong876 in Response to Salt Stress, International Journal of Molecular Sciences, May 7, 2022, pp. 1-16, vol. 23, 5231.

Xiaoduo Lu et al., Gene-Indexed Mutations in Maize, Molecular Plant, Mar. 2018, pp. 496-504, vol. 11.

* cited by examiner

SEQUENCE LISTING

```
Sequence total quantity: 5
SEQ ID NO: 1            moltype = DNA  length = 1878
FEATURE                 Location/Qualifiers
source                  1..1878
                        mol_type = other DNA
                        organism = Zea mays
SEQUENCE: 1
atgaagcgcg agtaccaaaa cgccggcggg aacgacggct acaggggctc ctccaaggac  60
aagtcgatgg cggcggcggc gggggcaggg gagcaggagg aggaggtgga cgagctgctg  120
```

```
gcggcgctcg ggtacaaggt gcgttcgtcg gatatggcgg acgtcgcgca gaagctagag    180
cagctcgaga tggccatggg gatgggcggc gcctgcccca ccgctgatga cgggttcgtc    240
tcgcacctcg ccacggacac cgtgcactac aatccctccg acctgtcgtc ctgggtcgag    300
agcatgctgt ccgagctcaa cgcgccccgg ccgccgctcc cacccgcgac gccggcacca    360
aggctggcgt ccacctcgtc caccgtcaca agtggcgccg ccgccggtgc cggctacttc    420
gatctcccgc ccgccgtcga ctcgtccagc agtacctacg ctctgaagcc gatccctcg    480
ccggtggcgg cggcgtcggc cgacccgtcc ccggactcgg cgcgggagcc caagcggatg    540
cgaactggcg gcggcagcac gtcgtcgtcc tcttcctcgt cgtcatccat ggacggcggc    600
cgcactagga gctccgtggt cgaagctgcc ccgccggcga cgcaggcggc caacgggccg    660
gcggtgccgg tggtggtggt ggacacgcag gaggccggga tccggctggt gcacgcgctg    720
ctggcgtgcg cggaggccgt gcagcaggag aacttctctg cggcggacgc gctggtgaag    780
cagatccccg tgctggcctc gtcgcagggc ggcgccatgc gcaaggtcgc cgcctacttc    840
ggcgaggcgc tcgcccggcg cgtgtatcgc ctccgcccgg caccggacgg ctccctcctc    900
gacgccgcct tcgccgacct cctgcacgcg cacttctacg agtcctgccc ctacctcaag    960
ttcgcccact tcaccgcgaa ccaggccatc ctcgaggctt tcgccgggtg ccgccgcgtc   1020
cacgtcgtcg acttcggcat caagcagggg atgcagtggc cggctctcct ccaggccctc   1080
gccctccgcc ccggcggccc ccgtcgttc cgtctcaccg gcgtaggccc gccgcagccc   1140
gacgagaccg acgccctgca gcaggtgggc tggaagctcg cccagttcgc gcacaccatc   1200
cgcgtcgact tccagtaccg tggcctcgtc gccgccacgc tcgctgacct ggagccgttc   1260
atgctgcgac cggagggcgg cggcgacacg gacgacgagc ccgaggtgat cgccgtaaac   1320
tcggtgtgcg agctgcaccg gctgctcgcg cagcccggta cactcgacaa ggtcctgggc   1380
accgtgcgcg cggtgcggcc gaggatcgtg acggtggtgg agcaggaggc caaccacaac   1440
tccggcacat tcctcgaccg cttcacggag tcgctgcact actactccac catgttcgac   1500
tccctcgagg gcgccggctc aggctccggc tccggctccg gctccggcca gcccaccgac   1560
gcctccccgc cggccgcac ggaccaggtg atgtccgagg tgtacctcgg ccggcagatc   1620
tgcaacatcg tggcgtgcga gggcgccgag cgcacggagc gccacgagcg gctggtccag   1680
tggcgcggcc gcctcggcgg gtccgggttc gagcccgtgc acctgggatc caacgcctac   1740
aagcaggcaa gcacgctgct ggccctcttc gccggcggc acgggtacag ggtggaggag   1800
aaggacgggt gcctgactct gggatggcat acgcgcccgc tcatcgccac ctcggcgtgg   1860
cgcgtcgccg ctccgtga                                                 1878

SEQ ID NO: 2            moltype = DNA  length = 1878
FEATURE                 Location/Qualifiers
source                  1..1878
                        mol_type = other DNA
                        organism = Zea mays
SEQUENCE: 2
atgaagcgcg agtaccaaaa cgccggcggg aacgacggct acaggggctc ctccaaggac     60
aagtcgatgg cggcggcggc gggggcaggg gagcaggagg aggaggtgga cgagctgctg    120
gcggcgctca ggtacaaggt gcgttcgtcg gatatggcgg acgtcgcgca gaagctagag    180
cagctcgaga tggccatggg gatgggcggc gcctgcccca ccgctgatga cgggttcgtc    240
tcgcacctcg ccacggacac cgtgcactac aatccctccg acctgtcgtc ctgggtcgag    300
agcatgctgt ccgagctcaa cgcgccccgg ccgccgctcc cacccgcgac gccggcacca    360
aggctggcgt ccacctcgtc caccgtcaca agtggcgccg ccgccggtgc cggctacttc    420
gatctcccgc ccgccgtcga ctcgtccagc agtacctacg ctctgaagcc gatccctcg    480
ccggtggcgg cggcgtcggc cgacccgtcc ccggactcgg cgcgggagcc caagcggatg    540
cgaactggcg gcggcagcac gtcgtcgtcc tcttcctcgt cgtcatccat ggacggcggc    600
cgcactagga gctccgtggt cgaagctgcc ccgccggcga cgcaggcggc caacgggccg    660
gcggtgccgg tggtggtggt ggacacgcag gaggccggga tccggctggt gcacgcgctg    720
ctggcgtgcg cggaggccgt gcagcaggag aacttctctg cggcggacgc gctggtgaag    780
cagatccccg tgctggcctc gtcgcagggc ggcgccatgc gcaaggtcgc cgcctacttc    840
ggcgaggcgc tcgcccggcg cgtgtatcgc ctccgcccgg caccggacgg ctccctcctc    900
gacgccgcct tcgccgacct cctgcacgcg cacttctacg agtcctgccc ctacctcaag    960
ttcgcccact tcaccgcgaa ccaggccatc ctcgaggctt tcgccgggtg ccgccgcgtc   1020
cacgtcgtcg acttcggcat caagcagggg atgcagtggc cggctctcct ccaggccctc   1080
gccctccgcc ccggcggccc ccgtcgttc cgtctcaccg gcgtaggccc gccgcagccc   1140
gacgagaccg acgccctgca gcaggtgggc tggaagctcg cccagttcgc gcacaccatc   1200
cgcgtcgact tccagtaccg tggcctcgtc gccgccacgc tcgctgacct ggagccgttc   1260
atgctgcgac cggagggcgg cggcgacacg gacgacgagc ccgaggtgat cgccgtaaac   1320
tcggtgtgcg agctgcaccg gctgctcgcg cagcccggta cactcgacaa ggtcctgggc   1380
accgtgcgcg cggtgcggcc gaggatcgtg acggtggtgg agcaggaggc caaccacaac   1440
tccggcacat tcctcgaccg cttcacggag tcgctgcact actactccac catgttcgac   1500
tccctcgagg gcgccggctc aggctccggc tccggctccg gctccggcca gcccaccgac   1560
gcctccccgc cggccgcac ggaccaggtg atgtccgagg tgtacctcgg ccggcagatc   1620
tgcaacatcg tggcgtgcga gggcgccgag cgcacggagc gccacgagcg gctggtccag   1680
tggcgcggcc gcctcggcgg gtccgggttc gagcccgtgc acctgggatc caacgcctac   1740
aagcaggcaa gcacgctgct ggccctcttc gccggcggc acgggtacag ggtggaggag   1800
aaggacgggt gcctgactct gggatggcat acgcgcccgc tcatcgccac ctcggcgtgg   1860
cgcgtcgccg ctccgtga                                                 1878

SEQ ID NO: 3            moltype = DNA  length = 439
FEATURE                 Location/Qualifiers
source                  1..439
                        mol_type = other DNA
                        organism = Zea mays
SEQUENCE: 3
gagctcggac agcatgctct cgacccagga cgacaggtcg gagggattgt agtgcacggt     60
gtccgtggcg aggtgcgaga cgaacccgtc atcagcggtg gggcaggcgc cgcccatccc    120
catggccatc tcgagctgct ctagcttctg cgcgacgtcc gccatatccg acgaacgcac    180
```

```
cttgtacccg agcgccgcca gcagctcgtc cacctcctcc tcctgctccc ctgccccgc    240
cgccgccgcc atcgacttgt ccttggagga gccctgtag ccgtcgttcc cgccggcgtt    300
ttggtactcg cgcttcatga tctcggagct acaggccggg ctagccagct aataattgct   360
tgcgcccctc cgtatcggtt ccgggatagc ttgggatttg gatccagggt tgggaattgg   420
gagttgggaa ggaaacgga                                                439

SEQ ID NO: 4            moltype = DNA  length = 20
FEATURE                 Location/Qualifiers
source                  1..20
                        mol_type = other DNA
                        organism = synthetic construct
SEQUENCE: 4
gagctcggac agcatgctct                                               20

SEQ ID NO: 5            moltype = DNA  length = 24
FEATURE                 Location/Qualifiers
source                  1..24
                        mol_type = other DNA
                        organism = synthetic construct
SEQUENCE: 5
tccgtttcct tcccaactcc caat                                          24
```

SEMI-DOMINANT MOLECULAR MARKER RELATED TO MAIZE DWARF AND APPLICATION THEREOF

CROSS-REFERENCE TO RELATED APPLICATIONS

The present application is a continuation application of PCT application No. PCT/CN2023/099574 filed on Jun. 12, 2023, which claims the benefit of Chinese Patent Application No. 202211232107.X filed on Oct. 10, 2022. The contents of all of the aforementioned applications are incorporated by reference herein in their entirety.

REFERENCE TO SEQUENCE LISTING

The Sequence Listing XML file submitted via the USPTO Patent Center, with a file name of "Sequence_listing_RONDA-23012-USPT.xml", a creation date of Aug. 9, 2023, and a size of 9.0 KB, is part of the specification and is incorporated in its entirety by reference herein.

TECHNICAL FIELD

The present application relates to the technical field of maize molecular breeding, in particular to a semi-dominant molecular marker related to maize dwarf and an application thereof.

BACKGROUND

Maize is one of three important food crops in China, and occupies an extremely important position in industrial and agricultural production as well as national food security strategies. The yield of the maize is determined by the yield per plant and the planting density per unit area, and increasing the planting density is an effective way to improve the maize yield per unit area (Duvick, Maydica, 2005, 50(3): 193-202). Due to the increase in planting density, the competition for water, fertilizer, light and other resources among plants is intensified, and the risk of lodging is increased, thus higher requirements are put forward for the plant architecture of density-tolerant maize, in which the maize plant height is one of the important traits concerned in the density-tolerant plant architecture. Creating dwarf or semi-dwarf mutants, identifying relevant dwarf genes, and applying it to breeding are important ways to conduct the breeding of density-tolerant varieties.

By cloning the "green revolution gene" semi-dwarf1 (sd-1) gene and reduced height 1 (rht1) of rice and wheat and applying it to breeding, the yield of crops is greatly improved (Sasaki et. al., Nature, 2002, 416(6882):701-702; Peng et. al., Nature, 1999, 400(6741):256-261). At present, some dwarf mutants discovered are mainly related to various hormones, in which it is mainly related to gibberellin synthesis and signal transduction, such as rice OsKS1, SLR1, GID2 genes (Gomi et. al., Plant J, 2010, 37(4): 626-634; Margis-Pinheiro et. al., Plant Cell Rep, 2005, 23(12): 819-833; Ikeda et. al., Plant Cell, 2001, 13(5): 999-1010), and maize Dwarf3, An1 genes (Winkler et. al., Plant Cell, 1995, 7(8), 1307-1317; Bensen et. al., Plant Cell, 1995, 7(1), 75-84). However, although some dwarf mutants are significantly reduced in plant height, it has many adverse traits, such as significant yield loss, so it is difficult to directly apply for breeding. Therefore, identifying excellent dwarf mutants with potential of breeding application is the key to genetic improvement of maize plant height and density-tolerant breeding.

SUMMARY

A purpose of the present application is to provide a semi-dominant molecular marker related to maize dwarf and an application thereof, and to provide a new breeding pathway with more potential for genetic improvement of maize plant height and density-tolerant breeding.

The present application is achieved by the following technical schemes.

The present application provides a semi-dominant molecular marker related to maize dwarf, the molecular marker is caused by a non-synonymous mutation from G to A in a maize gene Zm00001d013465, the molecular marker is a nucleotide sequence composed of the non-synonymous mutation site and its upstream and downstream bases. Zm00001d013465 encodes a maize Dwarf9 gene, and has a nucleotide sequence as shown in SEQ ID NO. 1. The molecular marker related to the maize dwarf has a nucleotide sequence as shown in SEQ ID NO. 2, and the non-synonymous mutation site is located in the 130th site of SEQ ID NO. 1 or SEQ ID NO. 2, which is mutated from G of SEQ ID NO. 1 into A of SEQ ID NO. 2.

The present application further provides a specific primer for detecting the above molecular marker related to the maize dwarf, and its sequence is:

```
E5779-F:
                                    (SEQ ID NO: 4)
5'-GAGCTCGGACAGCATGCTCT-3';

E5779-R:
                                    (SEQ ID NO: 5)
5'-TCCGTTTCCTTCCCAACTCCCAAT-3'.
```

The present application further provides a method for identifying a molecular marker related to maize dwarf using the above primer, and it includes the following steps: a genomic DNA of maize plant to be identified is used as a template, PCR amplification is performed by using the primer to obtain an amplification product, the amplification product is sequenced, and the base type of the non-synonymous mutation site of the molecular marker is determined.

The present application further provides an application of the above molecular marker related to the maize dwarf in breeding a new variety of dwarf and density-tolerant maize. The molecular marker has semi-dominance in a maize plant, the molecular marker is introduced into a plant of a variety to be improved or an inbred line plant by a field breeding or molecular breeding technology and the like, a heterozygous dwarf plant with a genotype AG or a homozygous dwarf plant with a genotype AA is obtained, and the plant height satisfies: homozygous dwarf plant<heterozygous dwarf plant<maize plant to be improved.

As a further optimization scheme of the present application, a method for breeding a new variety of dwarf and density-tolerant maize using the field breeding technology includes the following steps: a parent of the variety to be improved is hybridized with a variety containing the molecular marker related to the maize dwarf, to obtain an $F_1$-generation heterozygous dwarf plant, the $F_1$-generation heterozygous dwarf plant is self-crossed or back-crossed, and the homozygous dwarf plant or the heterozygous dwarf plant is acquired by trait separating and screening. Further preferably, the variety containing the molecular marker related to the maize dwarf is the maize E5779 dwarf mutant.

As a further optimization scheme of the present application, a method for breeding a new variety of dwarf and density-tolerant maize using the molecular breeding technology includes the following steps: a gene editing technology is used to mutate a base of the non-synonymous mutation site of the molecular marker in the genome of the variety to be improved from G into A, to obtain a dwarf variety.

The principle of the present application is that: the present application identifies a dwarf mutant, coded as E5779, from an EMS mutation population with maize B73 as the genetic background. Compared with the maize B73 inbred line, the trait of the E5779 mutant is caused by 1 base change, and it has greater prospect for marker development, germplasm identification, and breeding application.

Compared to existing technologies, the present application has the following advantages.

The present application identifies the dwarf mutant E5779 from the EMS mutation population with maize B73 as the genetic background. By genome resequencing and Mutmap mapping, it is found that the mutant is caused by the non-synonymous mutation from G to A in the gene Zm00001d013465, the non-synonymous mutation has the semi-dominant characteristics, and may significantly reduce the height of $F_1$-generation plants. The molecular marker is developed based on this, and the analysis and utilization of E5779 are helpful to improve the maize plant height and density-tolerant breeding, which has an important breeding application potential. The molecular marker developed on the basis of E5779 has the semi-dominant characteristics for the maize plant height, and thus the new maize variety with lodging resistance or density tolerance is bred, which has significant application prospect in production.

DETAILED DESCRIPTION OF THE EMBODIMENTS

Unless otherwise specified, the methods used in this embodiment are conventional methods known to those skilled in the art, and the reagents and other materials used are commercially available products.

B73 and CM37 inbred lines of maize used in this experiment are provided by the National Engineering Laboratory of Crop Stress Resistance Breeding, School of Life Sciences, Anhui Agricultural University.

The E5779 maize dwarf mutant used in this experiment comes from the EMS mutant library (http://elabcaas.cn/memd/public/index.html#/pages/search/geneid), and is a dwarf mutant identified from an EMS mutation population with maize B73 as a genetic background. The plant height and ear height of the mutant plant are significantly reduced, and the stem is thickened. By genome resequencing and Mutmap mapping, it is found that the mutant is caused by the non-synonymous mutation from G to A in the gene Zm00001d013465, the E5779 mutant has the semi-dominant characteristics, and may significantly reduce the height of $F_1$-generation plants. Therefore, E5779 has the important breeding application potential for improving the plant height and density-tolerant breeding.

The content of the present application is described in detail below in combination with specific implementation modes.

1. Identification and Phenotypic Analysis of Dwarf Mutant E5779

After being self-crossed, the dwarf mutant E5779 is shown in the same experimental field with the maize B73 inbred line, and after two generations of self-crossing observation, it is found that the phenotype of the E5779 mutant is consistent and genetically stable. As shown in A of FIG. 1, compared to the wild-type B73 inbred line, the plant height, ear height and tassel length of the E5779 mutant are all significantly reduced, it is found that the E5779 stem is thickened, which indicates that it has the potential to increase the plant lodging resistance.

2. Genetic Analysis of Dwarf Mutant E5779

The E5779 mutant is hybridized with the B73 inbred line before being self-crossed, and an F2 population obtained from self-crossing is shown in an experimental field with uniform field conditions. Around 15 days after the flowering period, the separation of traits in the F2 population is investigated by using the plant height as the main trait. It is found from results that in the F2 population, there are three types of plant height phenotypes: high, medium, and low, which represent wild-type B73, B73×E5779 heterozygous genotype and E5779 mutation genetic background respectively (the phenotypes are shown in A of FIG. 1, the plant height and ear height of the $F_1$-generation hybridization of B73×E5779 are between the B73 and E5779 mutants, which indicates that the E5779 mutant has the semi-dominant characteristics and great breeding application potential), the ratio is 41:92:43, and the separation ratio conforms to 1:2:1 ($\chi^2=0.41<2\chi_{0.05}^2=5.99$), which indicates that the E5779 is controlled by a single gene.

Figure 1:
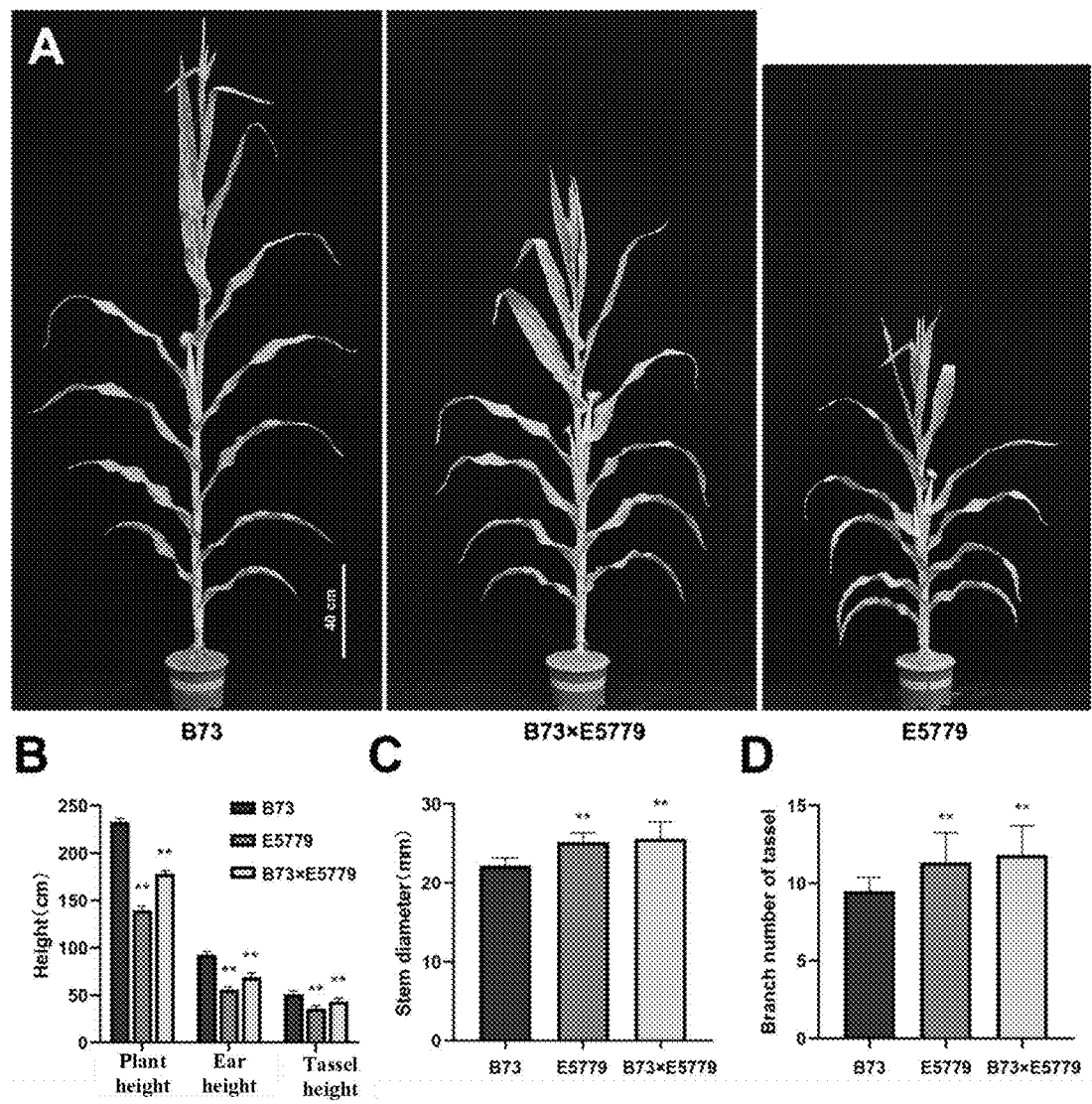
FIG. 1 shows phenotypic analysis of an E5779 mutant, and in the figure, A is plant phenotypes of wild-type B73 inbred line, B73×E5779 hybrid combination and E5779 mutant; B is statistics of plant height, ear height and tassel length of B73, E5779, and B73×E5779; C is statistics of stem diameter of the third internode above ground of B73, E5779, and B73×E5779; and D is statistics of tassel branch numbers of B73, E5779, and B73×E5779.

The plant height, ear height, tassel length, stem diameter of the third internode above ground, and tassel branching number of plants of wild-type B73, B73×E5779 heterozygous genotype and E5779 mutation genetic background are statistically analyzed, and results are shown in B-D of FIG. 1. The plant height, ear height, and tassel length of B73, B73×E5779, and E5779 are reduced sequentially, and the third internode stem diameter and tassel branching number of B73×E5779 and E5779 are significantly increased compared to B73.

3. Gene Mapping of Dwarf Mutant E5779

Figure 2:
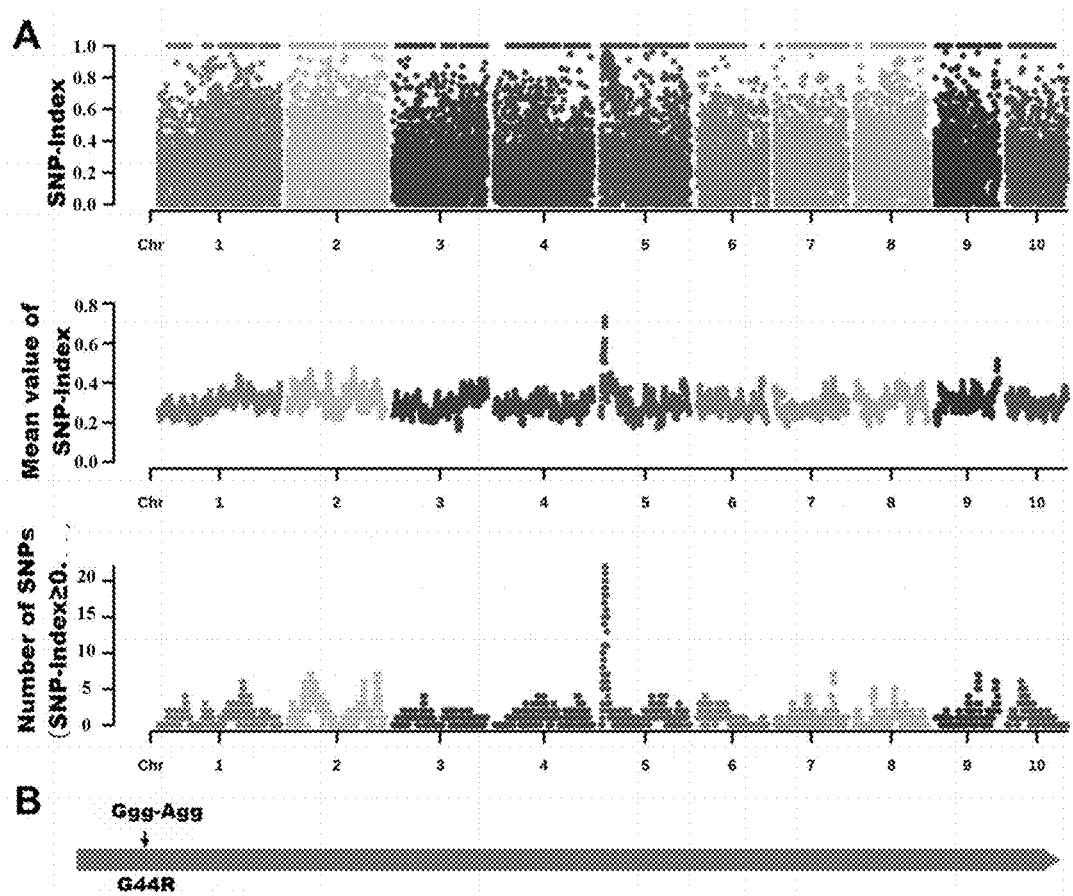
FIG. 2 shows gene mapping and position analysis of the E5779 mutant, and in the figure, A is identification to an SNP mutation site of the E5779 gene using a Mutmap mapping method; and B is structural analysis to the E5779 mutant gene.

From the self-crossed F2 separation population of B73× E5779, 19 mutant phenotype individual plants are selected, a Tiangen plant genome DNA extraction kit (DP305-03) is used to extract DNA respectively, and the specific operation process is shown in kit instructions. DNA integrity and concentration are measured by agarose gel electrophoresis and Qubit (Invitrogen, USA), and qualified DNA is used for subsequent analysis. DNA of each individual plant is mixed equally, 1 μg of the mixed DNA is taken for creating a library by using an Illumina TruSeq DNA library creating kit and sequenced by using an Illumina NovaSeq 6000 sequencer. The quality control is performed for the raw reads obtained from sequencing, to obtain clean reads. The published B73 genome (v4.32) is used as a reference genome, and a Mutmap mapping method is used to map a mutated gene (Lu et. al., Mol Plant, 2018, 11, 496-504). The identified single nucleotide polymorphism (SNP) is screened according to G→A (C→T) base mutation mode and SNP-Index=1.0 standard. On this basis, the variation type of the screened SNP is analyzed, and stop gained/lost, splice-site acceptor/donor, start gained/lost, and non-synonymous coding are screened. By calculating and analyzing the mean value of SNP-Index within the 3 Mb upstream and downstream range of each SNP, a significant SNP signal site interval is identified, and results are shown in FIG. 2. Furthermore, combined with the analysis to PCR amplification, Sanger sequencing verification, and functional annotation results and the like of the individual plant in the F2 separation population, it is determined that the E5779 mutant is caused by a non-synonymous mutation from G to A occurring in the gene Zm00001d013465 within this interval, Zm00001d013465 encodes the maize Dwarf9 gene, the mutation causes the 44th amino acid of Dwarf9 to change from glycine (G) to arginine (R), and the mutation is located within a DELLA domain.

4. Molecular Marker Design for Wild-Type and E5779 Mutant

The genomic DNA of wild-type B73 inbred line and E5779 mutant is extracted respectively by using an Aikorei plant genome kit, and used for subsequent PCR analysis after it is qualified by electrophoresis detection. According to the site of the E5779 mutant gene, a specific primer is designed to amplify a sequence length of 439 bp, as shown in SEQ ID NO. 3. The primer sequence is as follows:

```
SEQ ID NO. 4: E5779-F:
5'-GAGCTCGGACAGCATGCTCT-3'

SEQ ID NO. 5: E5779-R:
5'-TCCGTTTCCTTCCCAACTCCCAAT-3'.
```

Figure 3:
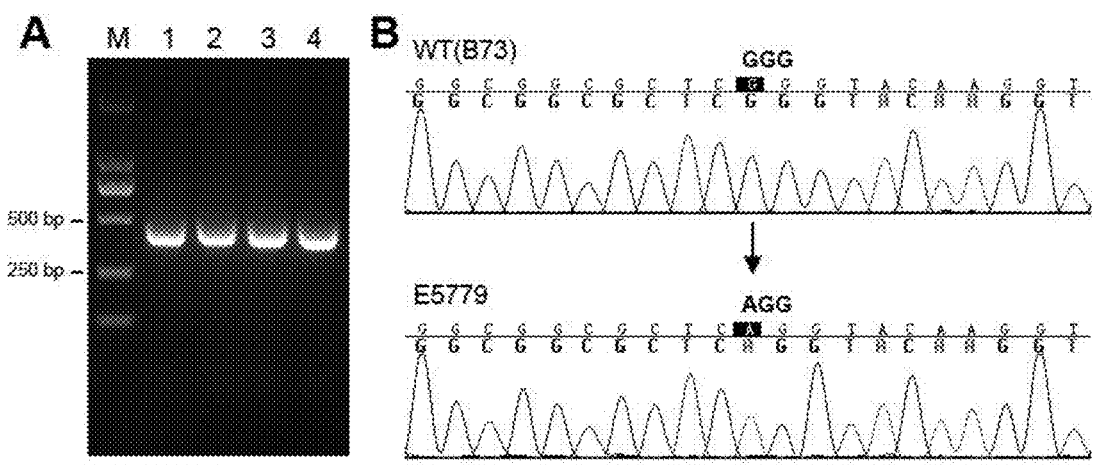
FIG. 3 shows development of a molecular marker for the E5779 mutant, and in the figure, A is wild-type and E5779 mutant PCR amplification electrophoresis analysis; M. Star-Marker D2000 Marker; 1-2, B73-1, and B73-2 amplified electrophoresis bands; 3-4, E5779-1, and E5779-2 amplified electrophoresis bands; and B is sequencing analysis of mutation sites in wild-type B73 and E5779 mutants.

A PCR amplification technology is used, and the specific primer is used to detect wild-type B73 and E5779 respectively. A PCR amplification system includes 12.5 μL of Taq Master Mix (2×), 1.0 μL of upstream and downstream primers, 2.0 μL of genomic DNA, and 8.5 μL of ddH$_2$O, and the total system is 25 μL. An amplification reaction procedure of PCR is as follows: it is pre-denatured at 95° C. for 5 min, denatured at 95° C. for 30 s, annealed at 65° C. for 30 s, extended at 72° C. for 40 s, totally extended at 72° C. for 10 min, and stored at 10° C. for 2 h. After the PCR reaction, 1.2% of agarose gel electrophoresis is used for detection. The size of a product is consistent with the size of a theoretical length, and the product is high in specificity and does not have a non-specific band. The PCR product is sent to a biological sequencing company for reverse primer sequencing, sequencing results are analyzed for the mutation site by using Sequencer software, the results show that the mutation site of the E5779 mutant is the base A, and the wild-type (B73) is the base G at the corresponding site (FIG. 3), which indicates that this marker may identify the wild-type and mutant genotypes and may be used for molecular breeding assisted molecular identification.

5. Breeding Application of E5779 Mutant

Figure 4:
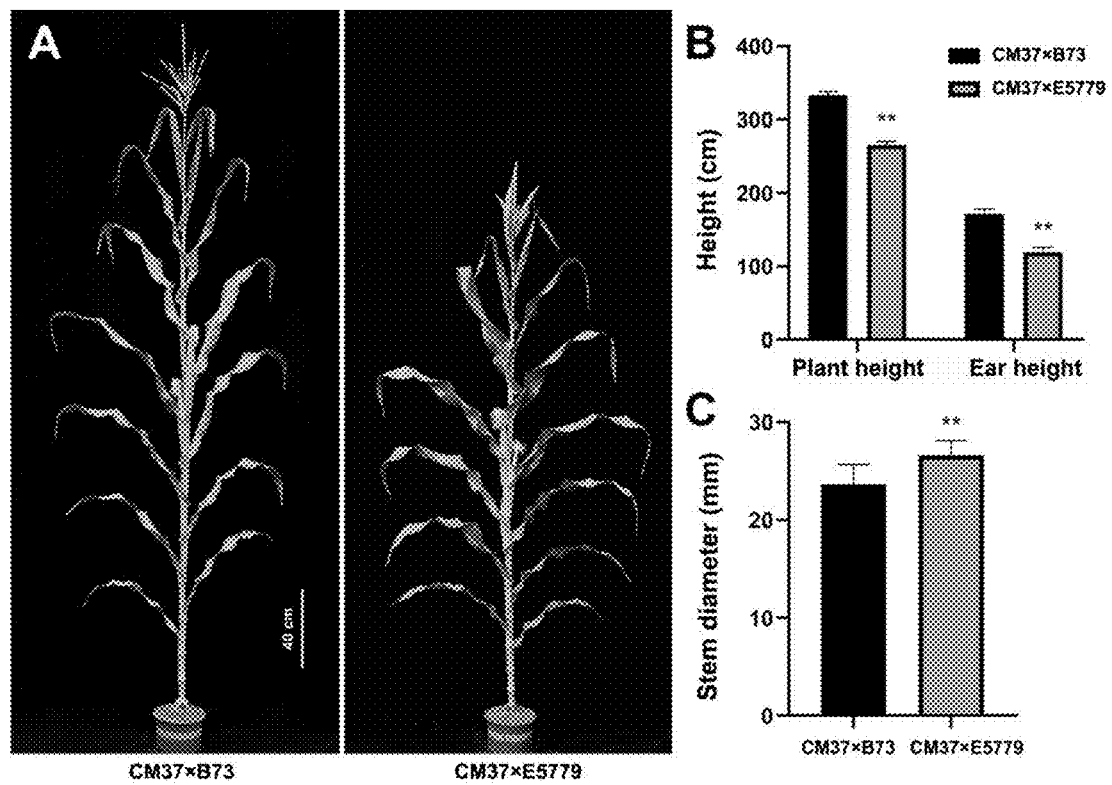
FIG. 4 shows phenotypic analysis of hybrid combinations prepared by the E5779 mutant, and in the figure, A is plant phenotype analysis of CM37×B73 and CM37×E5779 hybrid combinations; B is statistical analysis of plant height and ear height of the CM37×B73 and CM37×E5779 hybrid combinations; and C is statistical analysis of stem diameter of the third internode above ground of the CM37×B73 and CM37×E5779 hybrid combinations.
Figure 5:
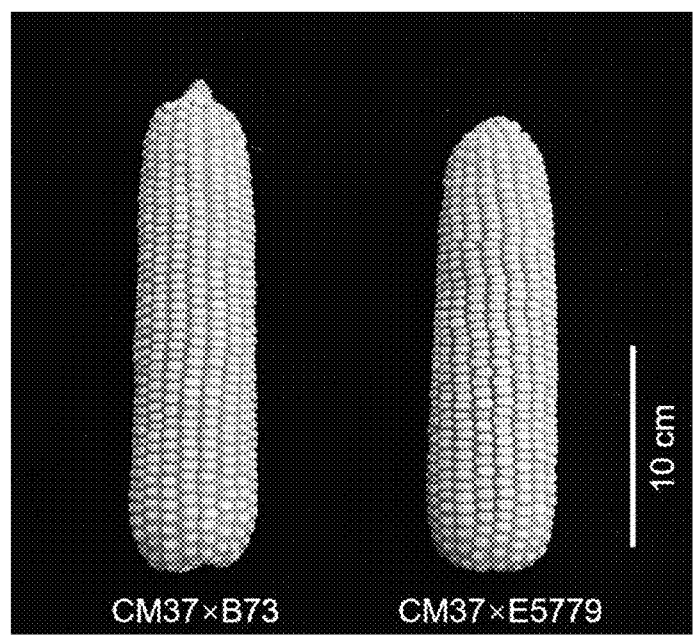
FIG. 5 shows ear phenotype of a breeding application of the E5779 mutant.

In order to evaluate the application of the E5779 mutant in breeding, the wild-type B73 and E5779 mutants are used as male parents, and hybridized respectively with a female parent CM37 (Xingen Zhang et. al., Comparative Transcriptomics Reveals the Molecular Mechanism of the Parental Lines of Maize Hybrid An'nong876 in Response to Salt Stress, Int J Mol Sci, 2022, 23, 5231.) of a new maize variety An'nong 876 (variety certification number: Guoshenyu 2020305) bred by the applicant, and then its phenotype is statistically analyzed. Results are shown in FIGS. 4 and 5, and FIG. 4 shows that compared to the CM37×B73 hybridized combination, the plant height (average decrease of 20.2%) and ear height (average decrease of 30.5%) of the CM37×E5779 hybridized combination are significantly reduced, and the improvement of the plant height and ear height traits is relatively ideal. It further indicates that the mutant may reduce the plant height of the $F_1$-generation and have the semi-dominant characteristics. At the same time, the stem of the CM37×E5779 hybridized combination is thickened. FIG. 5 shows that compared to the CM37×B73 hybridized combination, the CM37×E5779 hybridized combination shows better performance in ear capping, grain plumpness, ear length and other aspects. It indicates that the dwarf molecular marker has a relatively small effect on the yield of the $F_1$ plant (CM37×E5779), and it is further proved that E5779 is a mutant with potential for maize density-tolerant breeding and has an industrial promotion prospect.

The above are detailed implementation modes and specific operation processes of the present application, and are implemented under the premise of technical schemes of the present application. However, the scope of protection of the present application is not limited to the above embodiments.

---

The invention claimed is:

1. A semi-dominant molecular marker for maize dwarf, wherein the molecular marker is caused by a non-synonymous mutation from G to A in a maize gene as shown in SEQ ID NO: 1, the molecular marker has the nucleotide sequence as shown in SEQ ID NO: 2, and the non-synonymous mutation site is located in the 130th site of SEQ ID NO: 1.

2. The molecular marker of claim 1, wherein the molecular is detected with the specific primers of:

```
E5779-F:
                                          (SEQ ID NO: 4)
5'-GAGCTCGGACAGCATGCTCT-3';
and E5779-R:
                                          (SEQ ID NO: 5)
5'-TCCGTTTCCTTCCCAACTCCCAAT-3'.
```

3. A method for identifying the molecular marker for maize dwarf of claim 2, comprising the following steps:
   i) extracting a genomic DNA from a maize plant to be identified;
   ii) performing a PCR amplification on the extracted genomic DNA with the primers to obtain an amplification product: sequencing the amplification product; and
   iii) analyzing the sequencing results to determine the presence of the non-synonymous mutation at the 130th site of the gene corresponding to SEQ ID NO:1, wherein the mutation changes the base from G to A.

4. A method for breeding a new variety of dwarf and density-tolerant maize plant, the method comprising:
   i) amplifying the molecular marker for maize dwarf of claim 1, wherein the molecular marker has semi-dominance in a maize plant; introducing into a plant of a maize variety to be improved by a field breeding or molecular breeding technology; and obtaining a heterozygous dwarf plant with a genotype AG or a homozygous dwarf plant with a genotype AA having a reduced plant height as compared to the maize plant to be improved, and wherein the molecular breeding technology comprises utilizing a gene editing technology to mutate a base of the non-synonymous mutation site of the molecular marker in the genome of the variety to be improved from G into A, to obtain a dwarf variety.

5. The method of claim 4, wherein the field breeding technology comprises: hybridizing a plant of the maize variety to be improved with a maize plant containing the molecular marker for maize dwarf, to obtain an F1 generation heterozygous dwarf plant; self-crossing or back-crossing the F1 generation heterozygous dwarf plant; and acquiring the homozygous dwarf plant or the heterozygous dwarf plant by trait separating and screening.

6. The method of claim 5, wherein the variety containing the molecular marker for maize dwarf is the maize E5779 dwarf mutant.

* * * * *